US010058445B2

(12) United States Patent
Pathak et al.

(10) Patent No.: US 10,058,445 B2
(45) Date of Patent: Aug. 28, 2018

(54) MOTION STABILIZATION BY A HANDHELD TOOL

(71) Applicant: Verily Life Sciences LLC, Mountain View, CA (US)

(72) Inventors: Anupam J. Pathak, Mountain View, CA (US); Dylan Owens, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 37 days.

(21) Appl. No.: 15/171,842

(22) Filed: Jun. 2, 2016

(65) Prior Publication Data

US 2017/0348127 A1   Dec. 7, 2017

(51) Int. Cl.
G05B 13/02 (2006.01)
A61F 4/00 (2006.01)

(52) U.S. Cl.
CPC .............. *A61F 4/00* (2013.01); *G05B 13/021* (2013.01)

(58) Field of Classification Search
CPC ........ A61F 4/00; A16F 7/1005; A61B 5/1101; A61B 5/6824; A47G 21/08; G05B 13/021
See application file for complete search history.

(56) References Cited

U.S. PATENT DOCUMENTS

| 5,630,276 A * | 5/1997 | Weinstein | A47G 21/02 30/324 |
| 6,234,045 B1 * | 5/2001 | Kaiser | F16F 7/1005 74/572.2 |
| 2003/0006357 A1 * | 1/2003 | Kaiser | F16F 7/1005 248/550 |
| 2005/0257381 A1 * | 11/2005 | Currie | A47G 21/02 30/324 |
| 2010/0228362 A1 | 9/2010 | Pathak et al. | |
| 2012/0179075 A1 | 7/2012 | Perry et al. | |
| 2013/0297022 A1 | 11/2013 | Pathak | |
| 2014/0052275 A1 | 2/2014 | Pathak | |
| 2014/0303660 A1 | 10/2014 | Boyden et al. | |
| 2015/0300394 A1 | 10/2015 | Pathak | |
| 2017/0020704 A1 * | 1/2017 | Wu | A61F 4/00 |

FOREIGN PATENT DOCUMENTS

WO   2015003133 A1   1/2015

OTHER PUBLICATIONS

PCT/US2017/032221—International Search Report and Written Opinion dated Jul. 6, 2017, 13 pages.

* cited by examiner

*Primary Examiner* — Thomas J Sweet
*Assistant Examiner* — Christie Bahena
(74) *Attorney, Agent, or Firm* — Christensen O'Connor Johnson Kindness PLLC

(57) ABSTRACT

Systems and methods for tracking unintentional muscle movements of a user and stabilizing a handheld tool while it is being used by the user are described. The method may include detecting motion of a handle of the handheld tool manipulated by a user while the user is performing a task with a user-assistive device attached to an attachment arm of the handheld tool. Furthermore, the method may include storing the detected motion in a memory of the handheld tool as motion data. The method may also include controlling, based on the motion data, a motion-generating mechanism of the handheld tool that moves the attachment arm relative to the handle in a single degree of freedom in a direction of the detected motion of the handle.

13 Claims, 4 Drawing Sheets

MOTION STABILIZATION BY A HANDHELD TOOL

TECHNICAL FIELD

This disclosure relates generally to unintentional muscle movements, and in particular but not exclusively, relates to tracking unintentional muscle movements of a user and stabilizing a handheld tool while it is being used by the user.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Currently, persons with chronic neurodegenerative diseases are typically medicated with drugs that vary in effectiveness. The alternative to pharmacological treatment is brain surgery, such as deep brain stimulation (DBS) surgery. Similar to pharmacological treatments, DBS surgery varies in its effectiveness while being invasive and dangerous. Both forms of treatment are therefore non-optimal for treating persons with chronic neurodegenerative diseases, especially with respect to performing daily activities.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus, system and process for tracking unintentional muscle movements of a user while using a handheld tool and stabilizing the handheld tool in one degree of freedom while the handheld tool is used to perform an ordinary activity, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
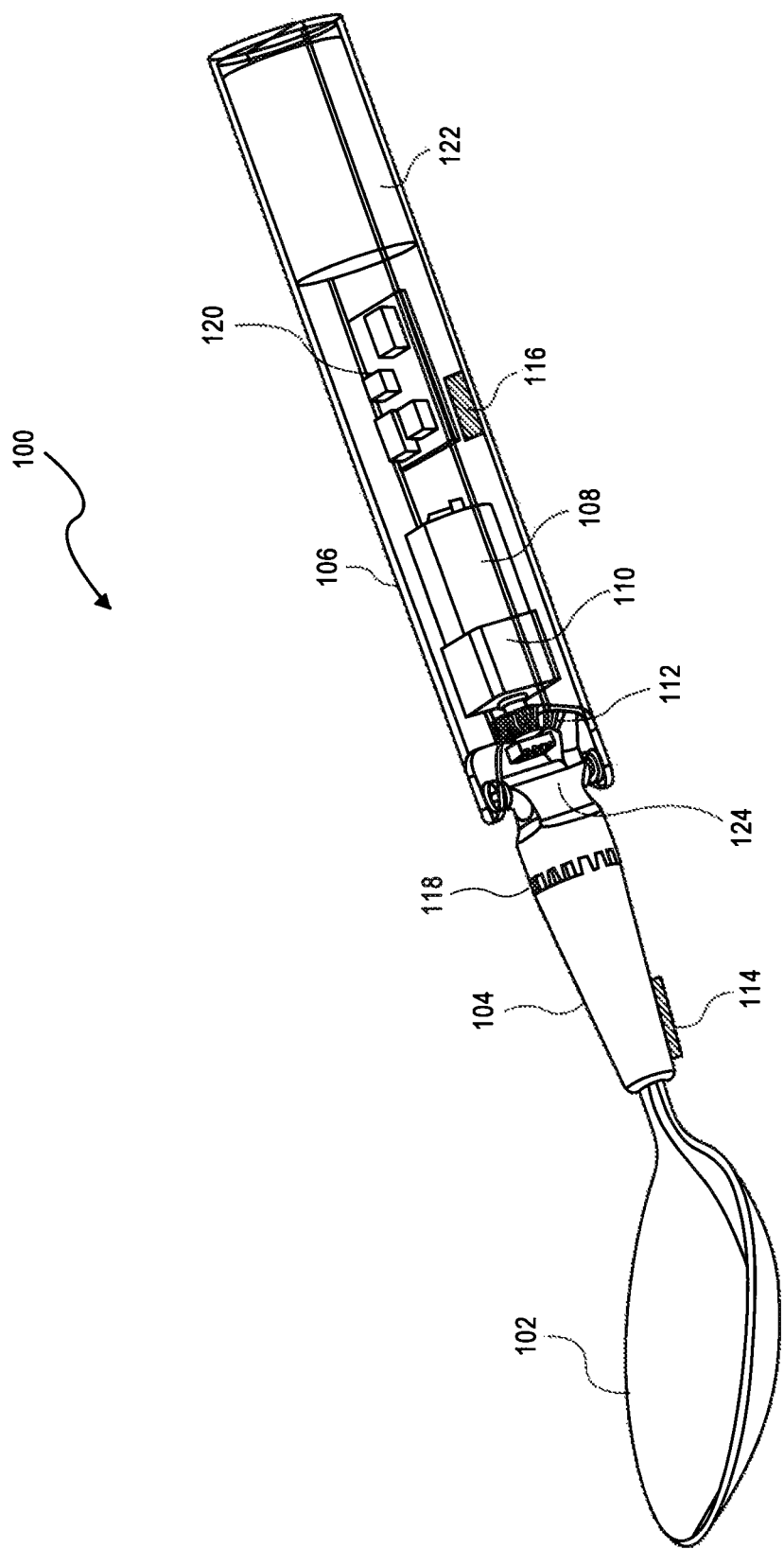
FIG. 1 is a perspective view illustration of a handheld tool that tracks unintentional muscle movements and performs motion stabilization in one degree of freedom, in accordance with an embodiment of the disclosure.

FIG. 1 illustrates a handheld tool 100 that tracks unintentional muscle movements and performs motion stabilization in one degree of freedom, in accordance with an embodiment of the disclosure. Handheld tool 100 is capable of detecting and compensating for unintentional muscle movement (e.g. tremors). Accordingly, the illustrated embodiment of handheld tool 100 includes a tremor tracking module 120 for measuring and tracking user tremors, as well as one or more sensors (e.g., sensor 114 and/or sensor 116) for providing signals to the tremor tracking module 120 for compensating for those same tremors, as discussed herein. These subsystems may have distinct components, or share some components such as power systems, memory, and may even share one or more sensors.

Handheld tool 100 includes a housing 106, which functions as a handle enabling a user to hold handheld tool 100. Handheld tool 100 also includes an attachment arm 104 coupled to the housing 106 via an indexer 118 on a pivot 124. Attachment arm 104 is configured to accept an implement 102 (e.g., a spoon in the illustrated embodiment) to its end distal from housing 106, with indexer 118 enabling the implement 102 to be rotatably attached to attachment arm. Handheld tool 100 further includes a tremor tracking module ("TTM") 120 for measuring and tracking tremors, as well as for controlling stabilization performed by the handheld tool using a motion generating mechanism (e.g., the actuator 108, gear reduction unit 110, and gear 112) discussed in greater detail below. One or more components of TTM 120 are rigidly attached to housing 106 to measure and track tremors of the handle that the user holds. FIG. 1 illustrates TTM 120 as a single component within housing 106; however, in other embodiments, TTM 120 includes several functional items that may assume a variety of different form factors and may further be spread throughout housing 106.

The illustrated embodiment of handheld tool 100 further includes at least one inertial sensor 114 placed along or within attachment arm 104 to measure movement of attachment arm 104 and user-assistive device/implement 102. In another embodiment, such as that illustrated in FIGS. 2A and 2B, the inertial sensor 114 may alternatively be placed on or within implement 102. In either embodiment, the at least one inertial sensor 114 sends motion signals back to TTM 120. In both embodiments, handheld tool 100 further includes a portable power source 122 to power the TTM 120 and actuator 108. In one embodiment, handheld tool 100 further includes at least one distributed motion sensor 116 for measuring relative motion of attachment arm 104 relative to housing 106, and also provides motion signals to TTM 120. In embodiments, one or more of the components for tracking tremor motions and/or performing motion stabilization may be omitted and/or positions of sensors changed while still implementing the tremor tracking and motion stabilization functionality disclosed herein. As examples, an inertial sensor may be placed along the attachment arm 104 and a position/angle sensor may be placed proximate to pivot 124, an inertial sensor may be placed along the attachment arm 104 and a second inertial sensor may be placed on or in housing 106, or an inertial sensor may be placed on or in housing 106 and a position/angle sensor may be placed proximate to pivot 124. In these embodiments, the combination of sensors and placement on handheld tool 100 enable TTM 120 to infer where attachment arm 104 and housing 106 are, and their positions relative to each other, for tremor tracking and motion compensation purposes. As another example, sensor 116 may be omitted, and tremor tracking and motion compensation performed using only sensor 114.

In one embodiment, attachment arm 104 is integrated with a specific type of implement 102 (e.g., a spoon as illustrated). In other embodiments, attachment arm 104 can receive a variety of different implements 102 in a variety of ways including but not limited to a friction, snap, or other form of locking mechanism. Power source 122 may utilize a variety of options including but not limited to a rechargeable battery, a solar panel, etc.

The at least one inertial sensor 114 and the at least one distributed motion sensor 116 detect unintentional muscle movements and measure signals related to these unintentional muscle movements that are created when a user adversely affects motion of implement 102. These sensors also detect the motion of the stabilized output relative to the housing 106. In one embodiment, the sensors (e.g., sensor 114 and 116) detect movements of the housing 106 in one degree of freedom (e.g., along a single axis). TTM 120 sends voltage commands in response to the detected motions along the one degree of freedom to the actuator 108. The voltage commands are chosen by TTM 120 to generate equal and opposite motions to the detected motions of housing 106 to stabilize implement 102 relative to the user's tremors or unintentional muscle movements in the detected one degree of freedom. The voltage commands are opposite in that they drive actuator 108 to generate motion of implement 102 in a direction opposite to the detected user motions. Furthermore, the voltage commands are equal in that they drive actuator to generate a motion of equal magnitude of the detected user motion. The equal and opposite motion of the implement 102 cancels out the user's unintentional motion thereby stabilizing the implement 102 relative to motion of the housing 106 by a user.

In one embodiment, stabilization of motion of handheld tool 100 in one degree of freedom may be beneficial for users whose unintentional muscle movements occur only, or substantially, along a single axis of movement. For example, a user's tremors may occur only, or substantially, in a vertical direction (e.g., up and down). Similarly, another user's tremors may occur only, or substantially, in a horizontal direction. Because the axis of a particular user's tremors may differ relative to usage orientation of implement 102, in one embodiment, handheld tool's 100 attachment arm 104 includes indexer 118 for rotatable attachment of implement 102 (e.g., implement 102 may be rotatably attached and/or rotated after attachment) to enable the one degree of freedom in which motion stabilization occurs to be altered. The implement 102 may be attached to attachment arm 104 and be continuously or discretely adjusted in 360 degrees using indexer 118. Indexer 118 enables the adjustment of implement 102 relative to attachment arm 104 when attached, and ensures that implement 102 remains fixed during motion stabilization using friction, magnet closure, complementary teeth, etc.

Figure 2A:
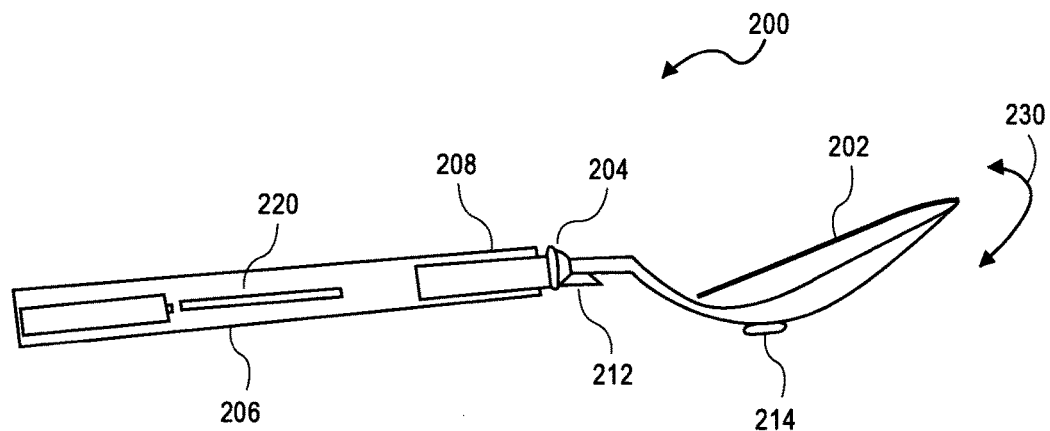
FIG. 2A is a perspective view illustration of a handheld tool that tracks unintentional muscle movements occurring in a first direction and performs motion stabilization in one degree of freedom in the first direction, in accordance with an embodiment of the disclosure.

FIG. 2A illustrates a handheld tool 200 that tracks unintentional muscle movements occurring in a first direction, and performs motion stabilization in one degree of freedom in the first direction. In one embodiment, the motion stabilization occurs in the first direction 230 in which the unintentional muscle movements occur. In embodiments, the direction of unintentional muscle movements of a user may be determined by a health professional that has diagnosed the user, by self-diagnosis of the user, by trial and error, or as detected by the TTM 220 of handheld tool 200 (e.g., feedback regarding motion of the user tracked by TTM 220). In the illustrated embodiment, where the first direction 230 of the unintentional muscle movements occur along a horizontal axis (e.g., horizontal motion of a user), implement 202 may be rotatably attached to attachment arm 204 so that actuator 208 can drive gear 212 along a single degree of freedom relative to the axis of unintentional muscle movement of the body 206. That is, the movement of the body in the first direction 230 may be detected using motion sensor 214 and TTM 220, as discussed herein. Based on the tracked movement, TTM 220 chooses voltage commands that generate signals to drive actuator 208 responsive to the detected movements to control the resulting motion of implement 202 along a single degree of freedom. In embodiments, the voltage commands can drive actuator 208 to control the resulting motion of implement 202 in an equal and opposite, and/or proportional, direction as the detected user movements. The resulting motion of implement 202 in the single degree of freedom stabilizes implement 202 relative to the motion of the body 206, therefore enabling a user to perform ordinary tasks using implement with reduced or no effects from the unintentional muscle movements.

Figure 2B:
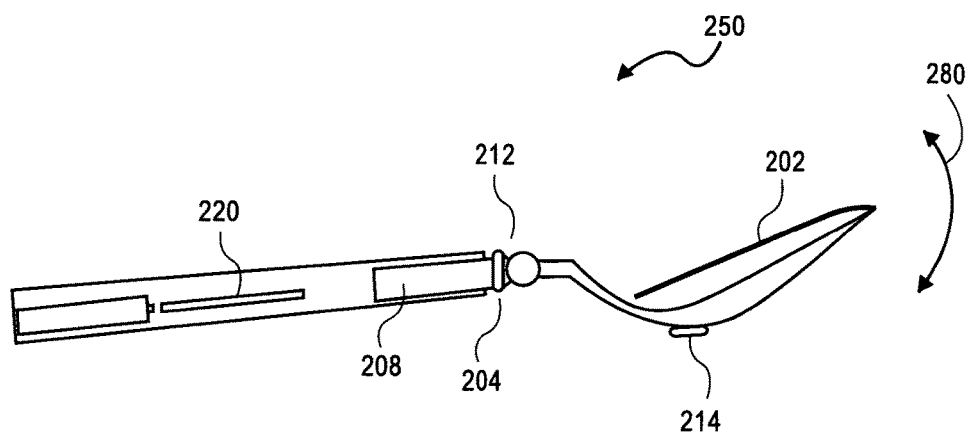
FIG. 2B is a perspective view illustration of a handheld tool that tracks unintentional muscle movements occurring in a second direction and performs motion stabilization in one degree of freedom in the second direction, in accordance with an embodiment of the disclosure.

FIG. 2B is another view of the handheld tool 200 that tracks unintentional muscle movements in a second direction 280. However, in contrast to FIG. 2A, the unintentional muscle movements of the user of handheld tool 200 occur in a second direction 280, such as along a vertical axis. Handheld tool 200 performs motion stabilization in one degree of freedom in the second direction, when implement's relative position with respect to attachment arm 204 is adjusted so that actuator 208 drives gear 212, as discussed herein, but the resulting motion of implement 202 occurs in one degree of freedom in the second direction 280. In the illustrated example, a user's vertical motion 280 would result in TTM 220 controlling vertical movement of implement 202 in one degree of freedom with motions equal and opposite to the tracked user motion. The result is the stabilization of implement 202 in response to unintentional muscle movements in the second direction.

The horizontal and vertical muscle movements of a user, and the motion stabilization performed by handheld tools 200 and 250 illustrated in FIGS. 2A and 2B, are illustrative. Motional stabilization of an implement of a handheld tool may occur in one degree of freedom in any orientation relative to the housing of the handheld tool. For example, users with tremors occurring along an axis of movement of, for example, 0°, 45°, 90°, 230°, etc., may also benefit from motion stabilization in one degree of freedom provided by the handheld tools discussed herein. These users would adjust, or have handheld tool adjusted for them, so that motion stabilization of the handheld tool's implement occurs in the appropriate one degree of freedom relative to the direction of the user's unintentional muscle movements.

Returning to FIG. 1, in one embodiment, the voltage commands generated by TTM 120 drive the actuator 108, which may be a motor, and turns the gear 112 through optional gear reduction unit 110. In embodiments, the voltage commands/signals turn gear 112 in an equal and opposite direction of detected unintentional muscle movements of a user. This cancellation maintains and stabilizes a position of the implement 102 in one degree of freedom, keeping it stable relative to the housing 106.

One of ordinary skill in the art readily recognizes that a system and method in accordance with the present disclosure may utilize various implementations of TTM 120, at least one inertial sensor 114, at least one distributed motion sensor 116, actuator 108 driving motion of attachment arm 104 in a single degree of freedom, etc. that would be within the spirit and scope of the present disclosure. In one embodiment, TTM 120 comprises an electrical system capable of producing an electrical response from sensor inputs such as a programmable microcontroller a field-programmable gate array (FPGA), an application specific integrated circuit ("ASIC"), or otherwise. In one embodiment, TTM 120 comprises an 8-bit ATMEGA8A programmable microcontroller manufactured by Atmel due to its overall low-cost, low-power consumption and ability to be utilized in high-volume applications.

In one embodiment, the at least one inertial sensor 114 is a sensor including but not limited to an accelerometer, gyroscope, or combination of the two. In one embodiment, the at least one distributed motion sensor 116 is a contactless position sensor including but not limited to a hall-effect magnetic sensor, a linear or rotary optical encoder sensor, a resistive potentiometer position sensor, a resolver sensor, etc.

One of ordinary skill in the art will readily recognize that an apparatus, a system, or method as described herein may be utilized for a variety of applications. For example, various different implements 102 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in not only improving the quality of life for the multitudes of individuals suffering from neurological motion disorders, but also in assisting in a variety of applications where physiological tremor is an issue including but not limited to manufacturing, surgical and public safety applications.

Furthermore, in the embodiments discussed herein, where motion of implement 102 is stabilized in one degree of freedom, the power needed to drive actuator 108 is reduced, and thus a smaller power source 122 may be used within handheld tool. Similarly, the control of implement's 102 motion in the one degree of freedom also utilizes a simpler motion control configuration (e.g., actuator 108, gear 112 and optional gear reduction unit 110), which again helps minimize the size of components of the handheld tool 100. The form factor of the body of housing 106 may therefore be reduced in size, resulting in a more conspicuous and user friendly motion stabilization device. Furthermore, assembly and construction of such a device are simplified resulting in reduced production time and costs. Finally, additional benefits, such as waterproofing may also be provided using the improved form factor of handheld tool 100.

Figure 3:
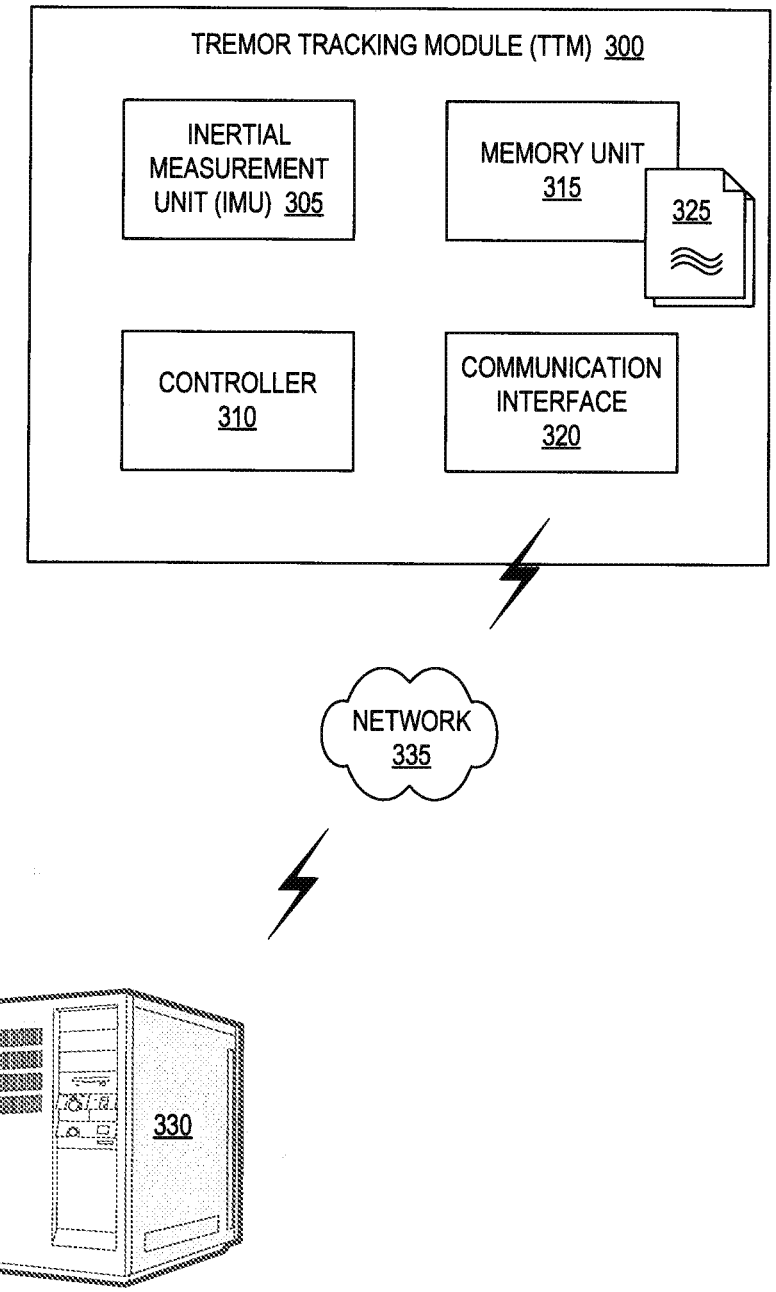
FIG. 3 is a functional block diagram illustrating a tremor tracking module, in accordance with an embodiment of the disclosure.

FIG. 3 is a functional block diagram illustrating a TTM 300, in accordance with an embodiment of the disclosure. TTM 300 is one possible implementation of TTM 120 illustrated in FIG. 1, and TTM 220 illustrated in FIGS. 2A and 2B. The illustrated embodiment of TTM 300 includes an inertial measurement unit ("IMU") 305, a controller 310, a memory unit 315, and a communication interface 320.

In one embodiment, IMU 305 is disposed in rigid contact with the housing of a handheld tool to directly measure the tremor motions of the handle and by extension the tremor motions of the user's hand. TTM 300 facilitates the measurement of human tremors while a user is performing an everyday task, such as eating or grooming (e.g., applying makeup). This is an important distinction over conventional in-clinic evaluations that simply measure the tremor of a hand that a patient is attempting to hold steady. Measurement and tracking of tremors while the patient is performing an everyday task measures the condition under real-world scenarios that are most adversely impacted by human tremors. Accordingly, TTM 300 can be embedded within everyday items or tools that are used routinely by patients to accurately measure and track their condition. This can lead to improved evaluations.

Not only can TTM 300 of a handheld tool measure and track human tremors during a routine task, but it can conveniently do so over a period of time to obtain a more reliable dataset for statistical analysis. Furthermore, the handheld tool including TTM 300 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of the patient's tremors facilitate improved treatments and interventions of the various diseases and the conditions that cause human tremors.

IMU 305 may be implemented using a variety of devices that measure motions of the handle of handheld tool 100. For example, IMU 305 may include one or more accelerometers that measure linear accelerations. In one embodiment, IMU 305 includes accelerometers capable of measuring translational accelerations of the handle in three orthogonal dimensions (e.g., x, y, and z dimensions). In one embodiment, IMU 305 includes a gyroscope to measure rotational motions (e.g., angular velocity about an axis) of the handle of handheld tool 100. In various embodiments, the gyroscope may be capable of measuring the rotational motions about one, two, or three orthogonal rotational axes. In one embodiment, IMU 305 includes a magnetometer to measure motions of the handle relative to a magnetic field (e.g., Earth's magnetic field or other externally applied magnetic field). In various embodiments, IMU 305 may include various combinations of some or all of the above listed motion measuring devices. Furthermore, these motion sensors may be disposed together on a common substrate that is rigidly attached to housing 106, or disposed throughout housing 106.

Controller 310 is communicatively coupled to IMU 305 and memory unit 315 to read motion data output from IMU 305 and store the motion data into memory unit 315. The motion data is collected over a period of time. For example, the motion data may be collected while the user performs an individual task, over the course of a day, a week, or other period of time. The collected motion data stored in memory unit 315 forms a motion log 325. In one embodiment, motion log 325 may contain enough information about the user's motions (linear accelerations, rotational velocities, durations of these accelerations/velocities, orientation relative to a magnetic field, etc.), based upon the motion data output from IMU 305, to recreate those motions using motion log 325. In one embodiment, motion log 325 may also record date/time stamps of when the motion data was collected and even include identifiers indicating the type of implement 102 that was attached to the handheld tool 100 when the motion data was collected. The type identifier provides an indication of the activity (e.g., eating with a fork, knife, or spoon, etc.) being performed by the user when the motion data was collected. This activity information and time/date stamps may be useful for the practitioner when evaluating the patient's motion log 325 to determine if the patient's tremors correlate to particular activities or time of day. In yet other embodiments, motion log 325 may also record battery voltage as a function of date/time, which may be used to analyzing system performance and battery usage. Tracking battery voltage is a sort of proxy for the amount of effort exerted by actuator 108 to stabilize implement 102. As such, tracking battery voltage or battery consumption correlates to the degree of a user's tremors since battery consumption will rise with increased tremors.

In one embodiment, controller 310 further provides signals to actuator 108 for controlling motion of implement 102. As discussed herein, the signals generated by controller 310 cause actuator to move implement 102 via gear 112 and gear reduction unit 110 in an equal and opposite direction as detected user motions of housing 106. As discussed herein, the movement of implement 102 occurs in one degree of freedom, where the one degree of freedom corresponds to an axis of detected user movement. Even though user movement is tracked relative to a single axis, and motion of implement 102 is stabilized in one degree of freedom, controller 310 may still collect motion data in additional axis for later analysis by a health profession, as discussed herein.

Controller 310 may be implemented with a programmable microcontroller, an FPGA, an ASIC, or other devices capable of executing logical instructions. The logical instructions themselves may be hardware logic, software logic (e.g., stored within memory unit 315 or elsewhere), or a combination of both. Memory unit 315 may be implemented using volatile or non-volatile memory (e.g., flash memory).

Communication interface 320 is communicatively coupled to output the motion log 325 from memory unit 315 to remote server 330 via network 335 (e.g., the Internet). In one embodiment, communication interface 320 is a wireless communication interface (e.g., Bluetooth, WiFi, etc.). For example, communication interface 320 may establish a wireless link to a user's cellular phone which delivers motion log 325 to server 330 via an installed tremor tracking application. The application may enable the user to control privacy settings, add comments about their usage of handheld tool 100, setup automatic periodic reporting of motion log 325, initiate a one-time reporting of motion log 325, determine a predominant direction of unintentional muscle movements detected by TTM 300, receive instructions or an indication as to how to set implement 102 relative to housing 106 to enable motion stabilization in a single degree of freedom, along with other user functions. In yet another embodiment, communication interface 320 may be a wired communication port (e.g., USB port). For example, when the user connects handheld tool 100 to a charging dock to charge power source 122, communication interface 320 may also establish a communication session with remote server 330 for delivery of motion log 325 thereto.

Figure 4:
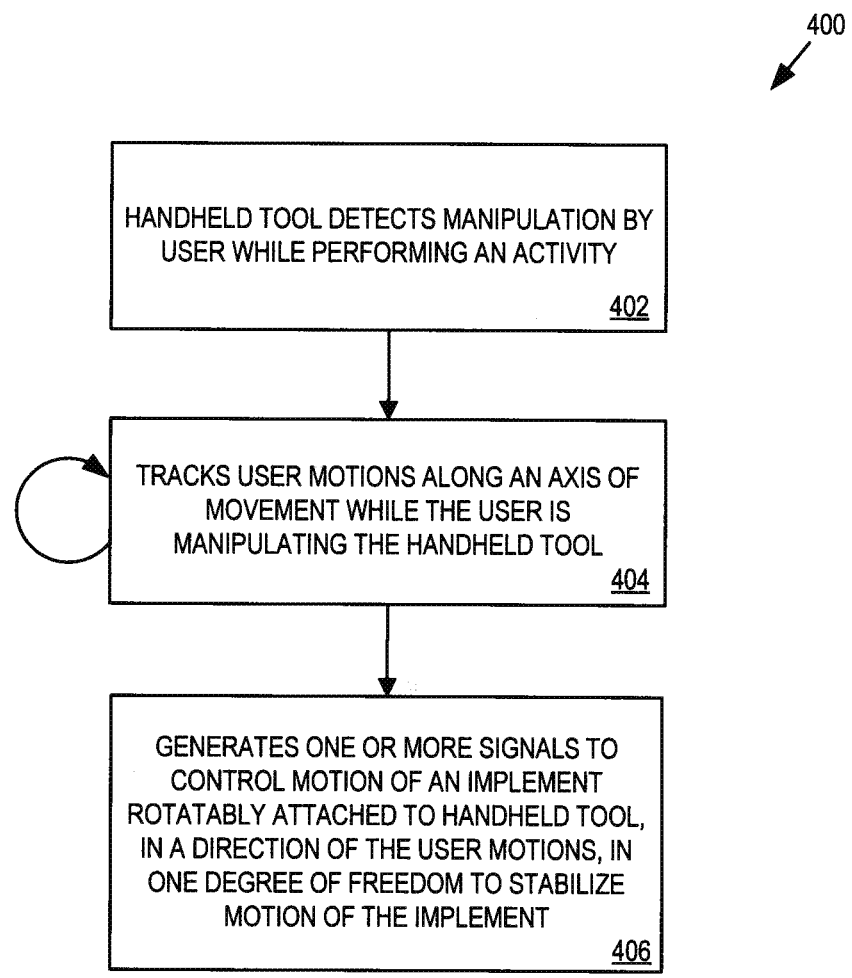
FIG. 4 is a flow chart illustrating a process for tracking unintentional muscle movements of a user while using a handheld tool and performing motion stabilization by the handheld tool, in accordance with an embodiment of the disclosure.

FIG. 4 is a flow chart illustrating a process 400 for tracking unintentional muscle movements of a user while using a handheld tool and performing motion stabilization by the handheld tool, in accordance with an embodiment of the disclosure. The process 400 is performed by processing logic that may comprise hardware (circuitry, dedicated logic, etc.), software (such as is run on a general purpose computer system or a dedicated machine), firmware, or a combination. In one embodiment, the process is performed by a tremor tracking module of a handheld tool (e.g., TTM 120 or 220). Furthermore, the order in which some or all of the process blocks appear in process 400 should not be deemed limiting. Rather, one of ordinary skill in the art having the benefit of the present disclosure will understand that some of the process blocks may be executed in a variety of orders not illustrated, or even in parallel.

The process begins by handheld tool detecting manipulation by a user while performing an activity (processing block 402). In one embodiment, the user uses the handheld tool (e.g., handheld tool 100, 200, 250) to perform a task or activity, such as a routine everyday activity including eating or grooming. Of course, handheld tool may also be used for other non-routine activities, as described above. In one embodiment, handheld tool detects the manipulation by detecting movement of the handheld tool based on measurements collected from one or more sensors of the handheld tool. Based on the detected manipulation by the user, handheld tool may transition from a lower power state to an operational state for performing motion stabilization, as discussed herein.

Processing logic tracks user motions along an axis of movement while the user is manipulating the handheld tool (processing block 404). In one embodiment, processing logic can detect motion of the handheld tool, and thus movement of a user, along a single axis of motion using measurements from one or more sensors, such as accelerometers, gyroscopes, gravitational sensors, etc. For example, processing logic can use sensor data to detect motions of a handheld tool in a vertical, horizontal, or any other direction. Processing logic continues to track user motions while the handheld tool is being manipulated by the user.

Processing logic generates one or more signals to control motion of an implement rotatably attached to handheld tool, in a direction of the user motions, in one degree of freedom to stabilize motion of the implement (processing block 406). As discussed herein, implement may be rotatably attached to an attachment arm of a handheld tool via an indexer, as discussed above. Based on how the implement is rotatably attached relative to a handle of the handheld tool (e.g., implement configured in a vertical, horizontal, or other orientation), the motion signals generated by processing logic will stabilize the implement in different directions, but always in one degree of freedom of movement.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A handheld tool, comprising:
   a handle;
   an implement;
   a motion generating mechanism at least partially disposed within the handle and mechanically coupled to the implement to move the implement relative to the handle in only a single degree of freedom;
   an indexer disposed between the motion generating mechanism and the implement, the indexer adapted to enable rotation of the implement relative to the handle when attaching the implement to change the single degree of freedom relative to the implement; and
   a tremor tracking module ("TTM") rigidly attached to the handle to detect a motion of the handle and configured to control the motion generating mechanism to move the implement relative to the handle in the single degree of freedom to stabilize the implement, wherein the indexer is adapted to hold a fixed rotational position during stabilization of the implement by the motion generating mechanism.

2. The handheld tool of claim 1, further comprising:
   an attachment arm disposed between the implement and the motion generating mechanism, wherein the implement is attached to a distal end of the attachment arm and the indexer is disposed along the attachment arm; and
   at least one sensor, coupled with the TTM, to detect tremor motions of the attachment arm and provide the detected tremor motions to the TTM.

3. The handheld tool of claim 2, wherein the at least one sensor comprise a first motion sensor and a second motion sensor, wherein the first motion sensor is disposed on the attachment arm to detect tremor motions of the attachment arm, and wherein the second motion sensor is disposed within the handle to detect relative motion of the attachment arm relative to the handle.

4. The handheld tool of claim 2, wherein the at least one sensor comprises one or more of an accelerometer, a gyroscope, magnetometer, or a combination thereof.

5. The handheld tool of claim 1, wherein the indexer includes complementary teeth that enable discrete rotational adjustments of the implement relative to the handle.

6. The handheld tool of claim 5, wherein movement of the implement resulting from user movement of the handle is stabilized by the motion-generating mechanism moving the attachment arm in a substantially equal magnitude but opposite direction of the detected motion of the handle.

7. The handheld tool of claim 1, wherein the indexer comprises a rotatable attachment point disposed between the implement and the motion generating mechanism.

8. The handheld tool of claim 1, wherein the implement comprises a kitchen utensil or a tool.

9. The handheld tool of claim 1, further comprising:
   a controller coupled to the TTM to read detected motion data;
   a memory unit coupled to the controller; and
   logic executable by the controller that when executed by the controller causes the handheld tool to perform operations comprising:
      generating a motion log within the memory unit based upon the detected motion while a user is holding the handheld tool; and
      periodically communicating the motion log to a remote server.

10. The handheld tool of claim 1, further comprising:
    an attachment arm disposed between the implement and the motion generating mechanism, wherein the implement is attached to a distal end of the attachment arm and the indexer is disposed along the attachment arm.

11. The handheld tool of claim 10, wherein the indexer comprises a connection point at which the implement is connected or disconnected from the attachment arm to mount different types of implements to the attachment arm at the connection point.

12. The handheld tool of claim 10, wherein the motion generating mechanism comprises:
    an actuator disposed in the handle;
    a gear reduction unit disposed in the handle and coupled to a first output of the actuator;
    a pivot coupled between gear reduction unit and the indexer; and
    a gear coupled between the pivot and the gear reduction unit, wherein a second output of the gear reduction unit is coupled to drive the gear and the gear is coupled to rotate the attachment arm about the pivot.

13. The handheld tool of claim 12, wherein the pivot rotates about a first axis that is perpendicular to a second axis about which the second output of the gear reduction unit rotates.

* * * * *